United States Patent [19]
Kriesel

[11] Patent Number: 5,741,242
[45] Date of Patent: Apr. 21, 1998

[54] INFUSION DEVICE WITH FILL ASSEMBLY

[75] Inventor: Marshall S. Kriesel, Saint Paul, Minn.

[73] Assignee: Science Incorporated, Bloomington, Minn.

[21] Appl. No.: 577,059

[22] Filed: Dec. 22, 1995

[51] Int. Cl.⁶ .................................................. A61B 19/00
[52] U.S. Cl. .......................... 604/403; 141/318; 604/406; 604/132
[58] Field of Search .................................. 604/131, 132, 604/151, 153, 181, 183, 187, 200, 201, 205, 218, 232, 403, 406, 415; 141/18, 318

[56] References Cited

U.S. PATENT DOCUMENTS

| | | |
|---|---|---|
| 4,048,997 | 9/1977 | Raghavachari et al. |
| 4,180,070 | 12/1979 | Genese ........................ 128/218 |
| 4,614,515 | 9/1986 | Tripp et al. .................... 604/403 |
| 4,883,483 | 11/1989 | Lindmayer .................... 604/411 |
| 4,886,495 | 12/1989 | Reynolds ....................... 604/88 |
| 4,919,657 | 4/1990 | Haber et al. .................. 604/232 |
| 5,067,948 | 11/1991 | Haber et al. .................. 604/213 |
| 5,112,307 | 5/1992 | Haber et al. .................. 604/110 |
| 5,137,511 | 8/1992 | Reynolds ....................... 604/88 |
| 5,171,214 | 12/1992 | Kolber et al. .................. 604/82 |
| 5,295,976 | 3/1994 | Harris ............................ 604/211 |
| 5,304,165 | 4/1994 | Haber et al. .................. 604/411 |
| 5,334,162 | 8/1994 | Harris ............................ 604/232 |
| 5,336,180 | 8/1994 | Kriesel et al. .................. 604/82 |
| 5,336,188 | 8/1994 | Kriesel .......................... 604/132 |
| 5,364,386 | 11/1994 | Fukuoka et al. .............. 604/411 |
| 5,374,256 | 12/1994 | Kriesel .......................... 604/232 |
| 5,397,303 | 3/1995 | Sancoff et al. ................. 604/82 |
| 5,405,326 | 4/1995 | Haber et al. .................. 604/110 |
| 5,411,480 | 5/1995 | Kriesel .......................... 604/133 |
| 5,451,214 | 9/1995 | Hajishoreh .................... 604/235 |
| 5,454,793 | 10/1995 | Levander et al. ............. 604/235 |
| 5,462,535 | 10/1995 | Bonnichsen .................. 604/272 |
| 5,466,220 | 11/1995 | Brenneman .................... 604/87 |
| 5,472,422 | 12/1995 | Ljungquist ..................... 604/89 |
| 5,484,406 | 1/1996 | Wong ............................. 604/87 |

*Primary Examiner*—Corrine M. McDermott
*Attorney, Agent, or Firm*—James E. Brunton

[57] ABSTRACT

A fluid delivery apparatus which includes a fluid delivery assembly and a unique fill assembly that can be used to controllably fill the fluid reservoir of the fluid delivery assembly in the field. The fill assembly includes a fluid containing vial assembly mounted within a unique adapter assembly which functions to conveniently mate the vial assembly with several different types of fluid delivery assemblies of the character that embody self-contained stored energy means.

23 Claims, 6 Drawing Sheets

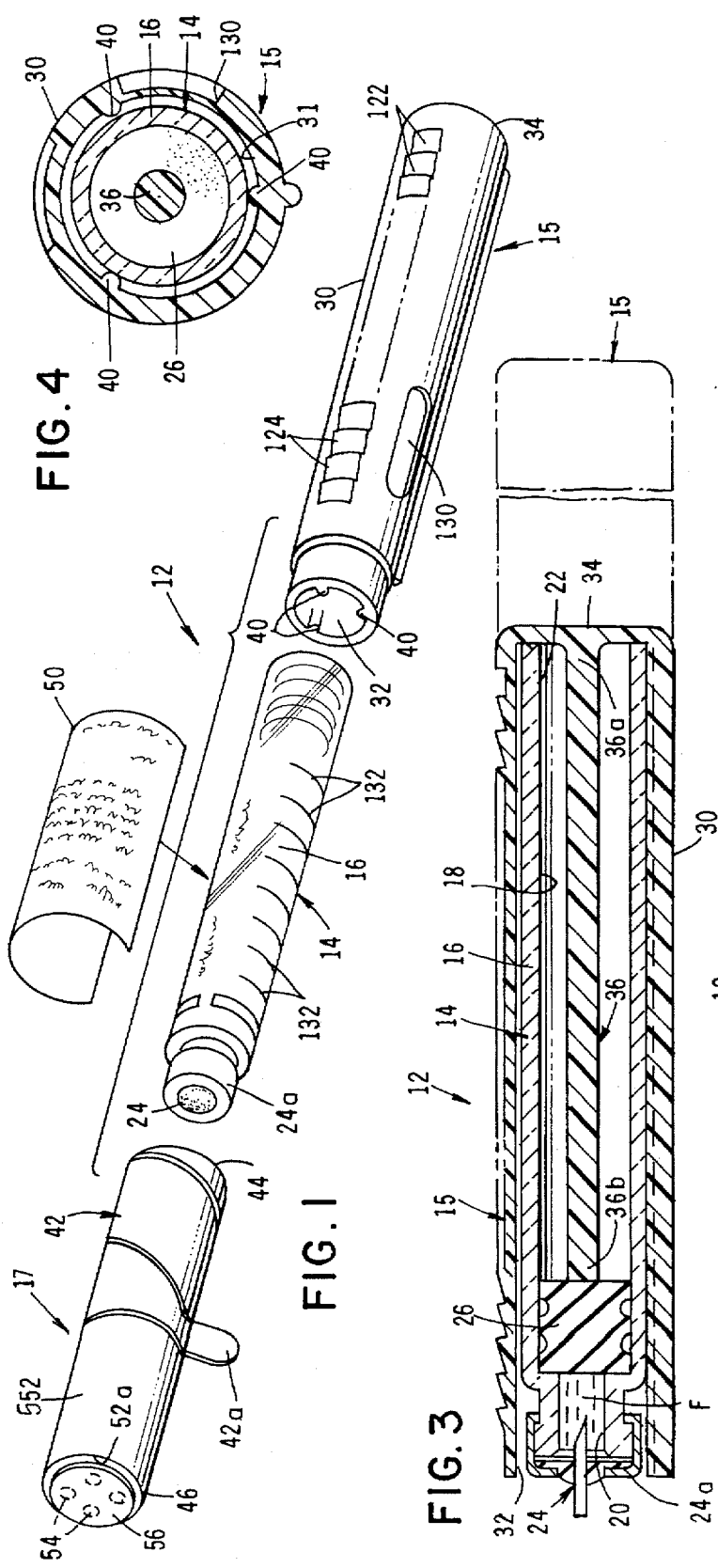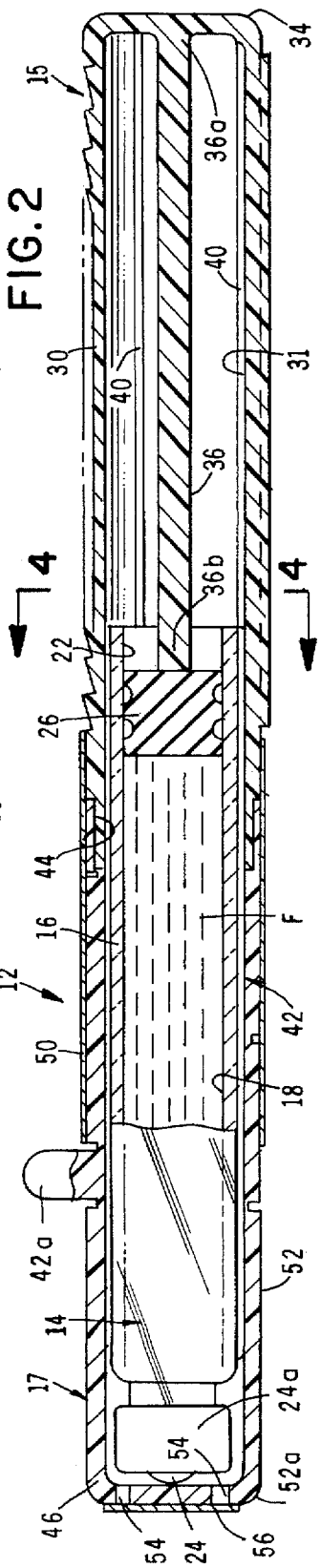

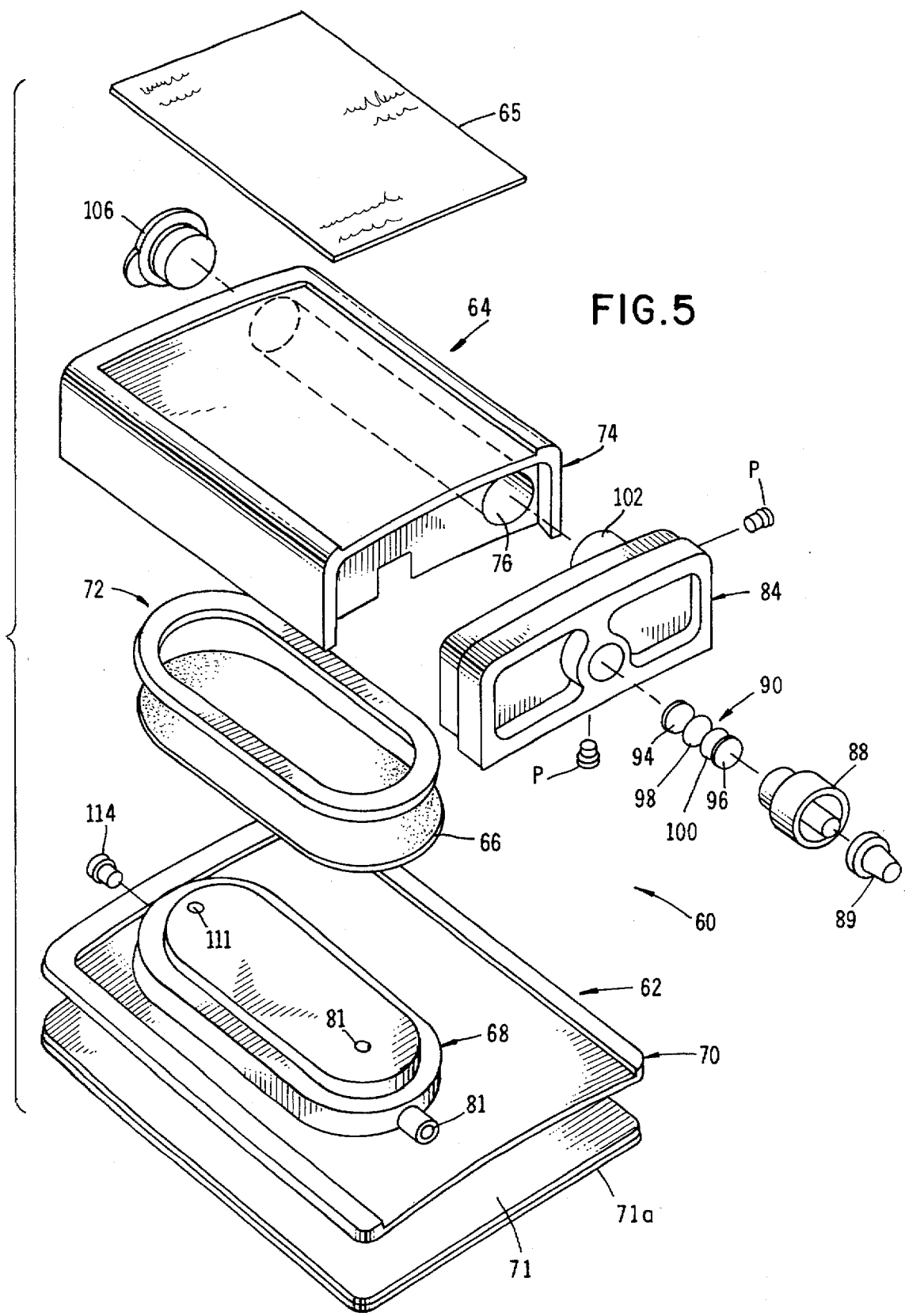

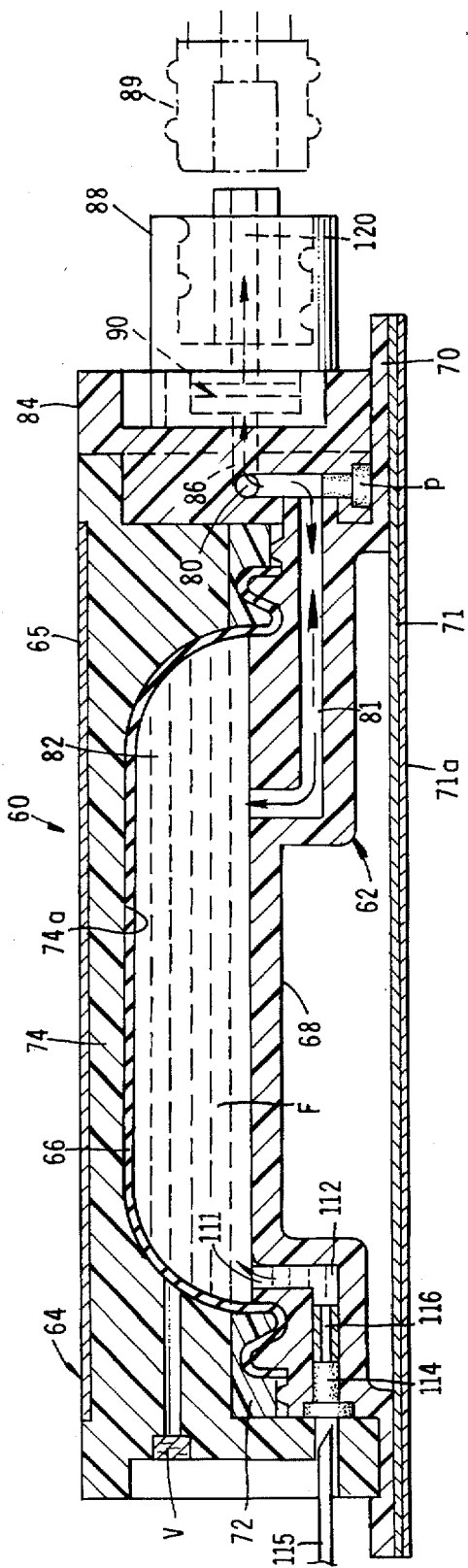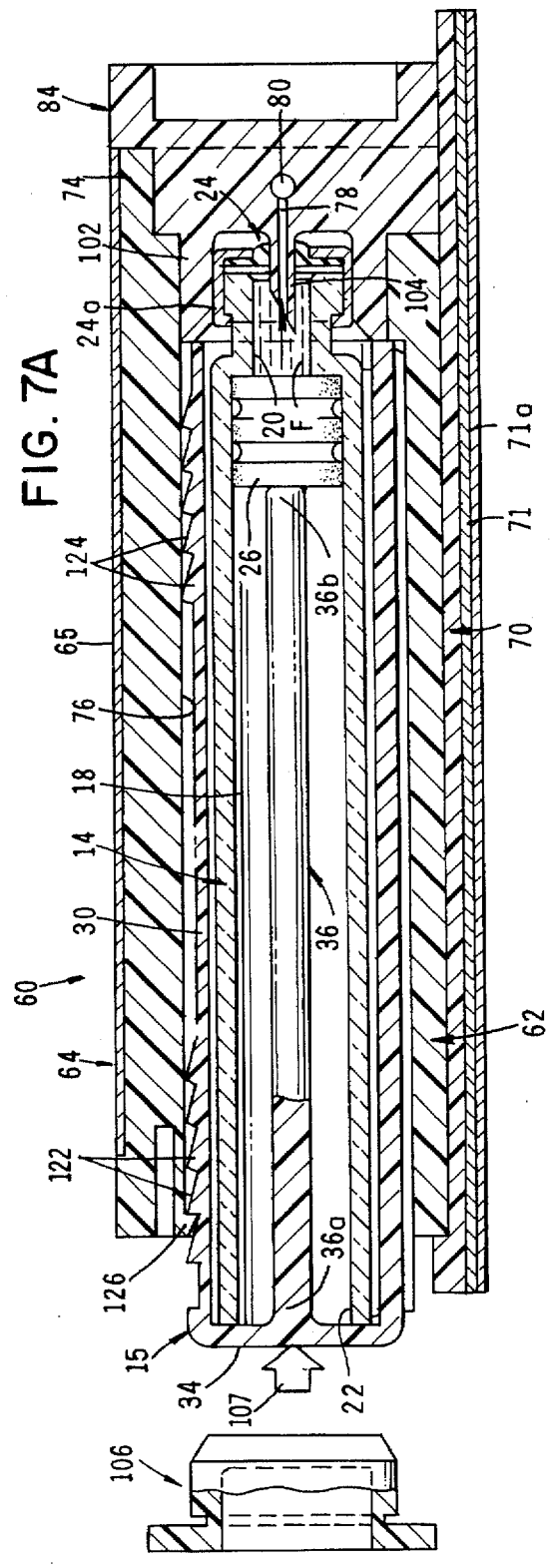
FIG. 7
FIG. 7A

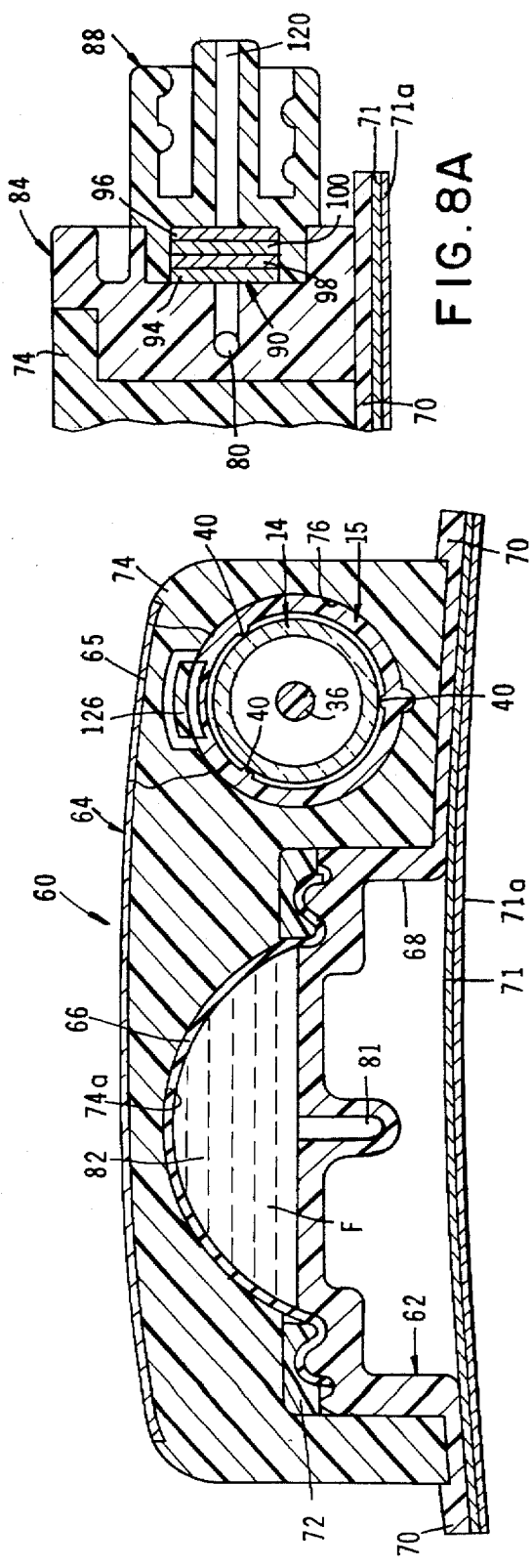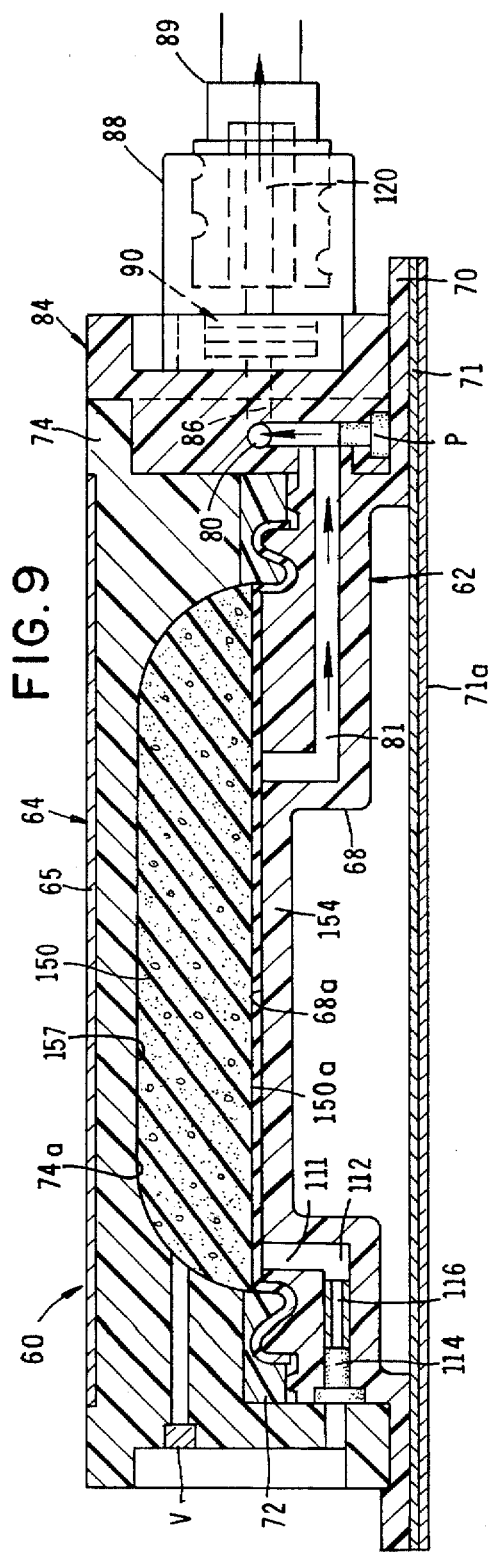

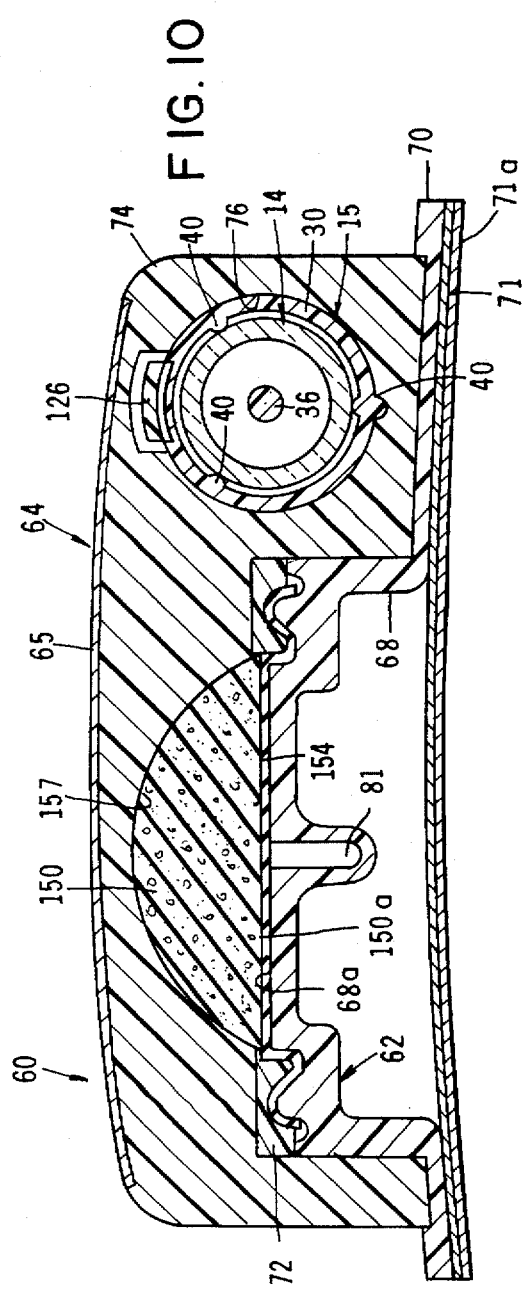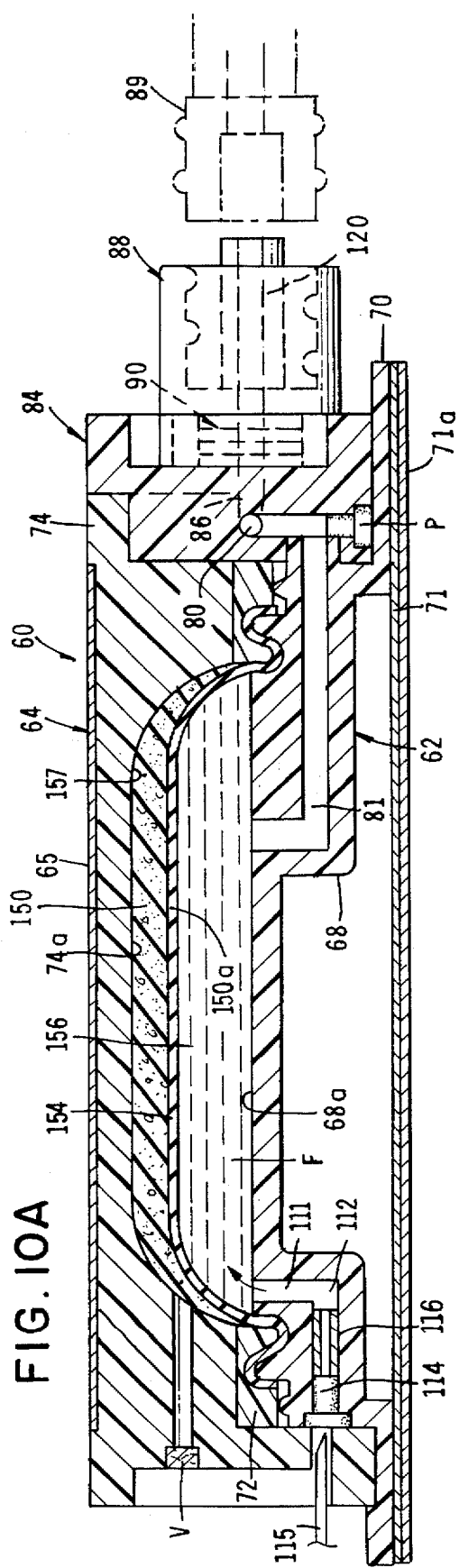

5,741,242

INFUSION DEVICE WITH FILL ASSEMBLY

BACKGROUND OF THE INVENTION

1. Field of the Invention

The present invention relates generally to fluid delivery devices for infusion of beneficial agents into a patient. More particularly, the invention concerns infusion devices which include a novel fill assembly for filling the fluid reservoir of the infusion devices.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by medicating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished by gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

To overcome the drawbacks of the prior art fluid delivery systems, the present inventor has devised a number of highly novel fluid delivery devices for use by ambulatory patients which embody self-contained stored energy means for delivering fluids from the reservoir of the device at precisely controlled rates. The devices employ various types of materials to construct the stored energy sources including elastomeric film materials and expandable cellular materials such as elastomeric foams. In these devices, after the fluid reservoir of the device has been filled, the elastomeric films or the expandable cellular materials, as the case may be, function to controllably force the fluid from the reservoir and outwardly of the device at precise rates. Exemplary of these novel fluid delivery devices are those disclosed in U.S. Pat. Nos. 5,205,820; 5,263,940; 5,279,558; 5,336,188; and 5,254,278 issued to the present inventor. Since U.S. Pat. No. 5,411,480 has particular relevance to the present invention, this patent is hereby incorporated by reference in its entirety as though fully set forth herein.

The devices described in the aforementioned patents can be used with minimal professional assistance in an alternate health care environment, such as the home. Certain of the devices can also be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately delivery fluids to the patient in precisely the correct quantities and at extended microfusion rate over time.

The thrust of the present invention is to provide a novel fluid delivery apparatus that includes a unique fill assembly that can be used to controllably fill the fluid reservoir of the apparatus in the field. As will be better understood from the description which follows, the fill assemblies of the present invention include a fluid containing vial assembly mounted within a unique adapter assembly which functions to conveniently mate the vial assembly with several different types of fluid delivery devices that embody self-contained stored energy means.

In use, the adapter assembly of the invention interconnects the fluid containing vial with the fluid delivery device so that the reservoir of the device can be controllably filled with the fluid contained within the vial assembly. After the reservoir is thus filled, the stored energy means of the fluid delivery device will function to controllably expel the fluid from the device.

SUMMARY OF THE INVENTION

It is an object of the present invention to provide a fluid delivery apparatus which embodies a stored energy source such as distendable elastomeric membrane or a compressible cellular mass and includes a unique fill assembly for use in controllably filling the fluid reservoir of the apparatus. The novel fill assembly of the invention is specially designed for use with various types of fluid delivery devices and enables the fluid reservoir of the devices to be aseptically filled in the field shortly before use with a wide variety of medicinal fluids.

Another object of the present invention is to provide an apparatus of the aforementioned character in which the fill assembly comprises a vial assembly of generally conventional construction that can be prefilled with a wide variety of medicinal fluids.

Another object of the present invention is to provide a fill assembly of the type described in the preceding paragraph in which the prefilled vial assembly is partially received within a novel adapter assembly that functions to operably couple the vial assembly with the fluid delivery device.

Another object of the invention is to include viewing means for viewing the amount of fluid remaining within the prefilled vial as the fluid reservoir is being filled.

Another object of the invention is to provide an adapter assembly of the type described in which the body of the prefilled vial is surrounded by a protective covering until immediately prior to mating the assembly with the fluid delivery device.

Another object of the invention is to provide an apparatus as described in the preceding paragraphs in which the adapter assembly includes locking means for locking the assembly to the fluid delivery device following filling of the fluid reservoir of the device.

Another object of the invention is to provide an adapter assembly of the character described that is highly versatile in that it can be used with a wide variety of fluid delivery devices.

Another object of the invention is to provide a novel adapter assembly which is easy to use, is inexpensive to manufacture, and one which maintains the prefilled vial in sterile condition until time of use.

BRIEF DESCRIPTION OF THE DRAWINGS

FIG. 1 is a generally perspective exploded view of one form of the adapter assembly of the present invention.

FIG. 2 is a enlarged, cross-sectional view of the adapter assembly illustrated in FIG. 1 as it appears in an assembled configuration.

FIG. 3 is a cross-sectional view similar to FIG. 2, but showing the appearance of the component parts of the invention after the plunger of the container has been telescopically moved from a first to a second position.

FIG. 4 is a cross-sectional view taken along lines 4—4 of FIG. 2.

FIG. 5 is a generally perspective, exploded view of one form of fluid delivery device of the invention with which the adapter assembly shown in FIG. 1 can be operably interconnected.

FIG. 7 is a cross-sectional view taken along lines 7—7 of FIG. 6.

FIG. 7A is a cross-sectional view taken along lines 7A—7A of FIG. 6.

FIG. 8 is a cross-sectional view taken along lines 8—8 of FIG. 6.

FIG. 8A is a cross-sectional view taken along lines 8A—8A of FIG. 6.

FIG. 9 is a cross-sectional view of an alternate form of fluid delivery device with which the adapter assembly of FIG. 1 can be operably associated.

FIG. 10 is a transverse cross-sectional view of the delivery device shown in FIG. 9.

FIG. 10A is a cross-sectional view similar to FIG. 9 but showing the compaction of the stored energy means of the device as the fluid reservoir is filled.

DESCRIPTION OF THE INVENTION

Figure 6:
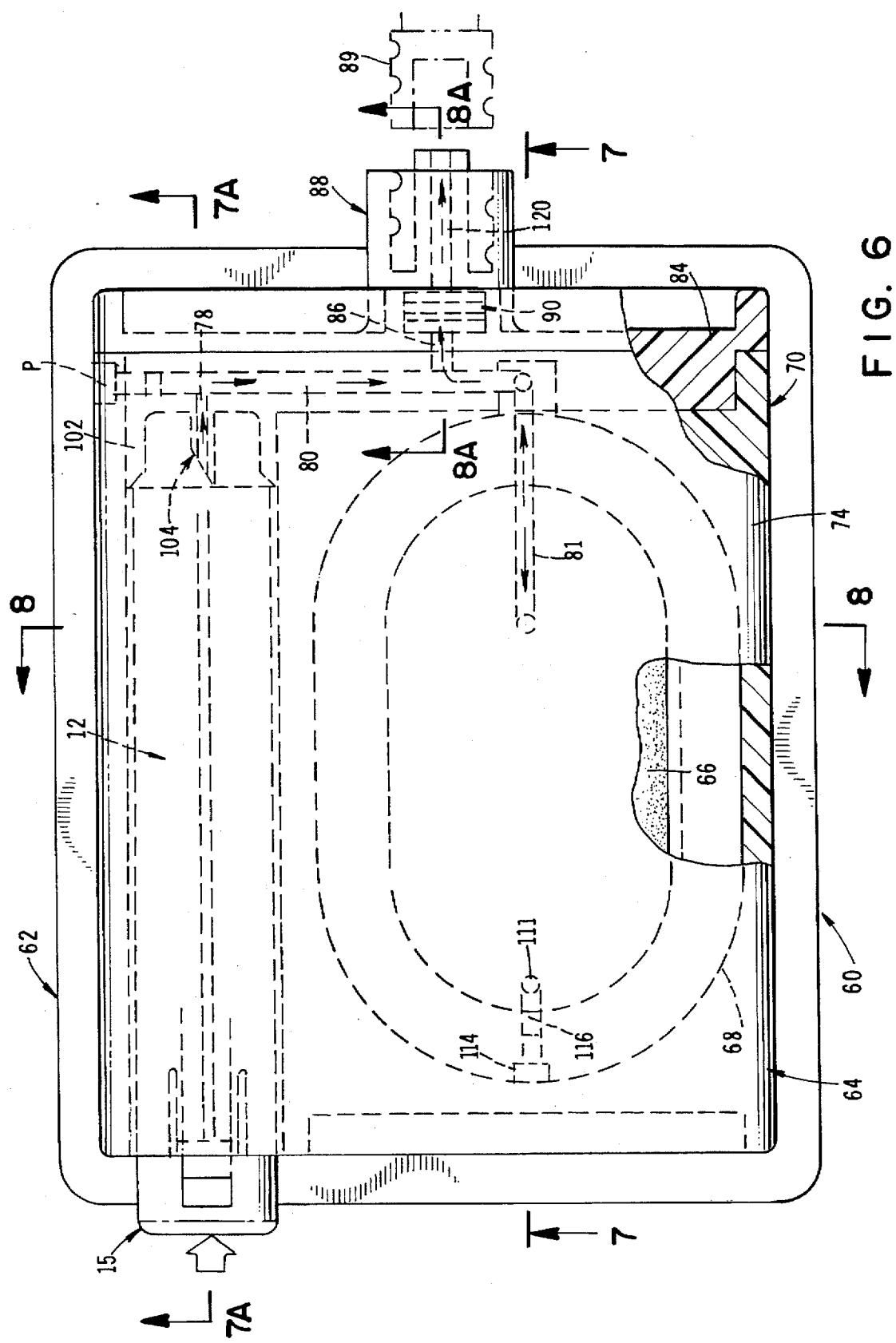
FIG. 6 is a plan view of the fluid delivery device shown in FIG. 5.

Referring to the drawings and particularly to FIGS. 1 through 4, one form of the fill assembly of the present invention is there illustrated and generally designated by the numeral 12. Fill assembly 12 is specially designed for use with fluid delivery apparatus of a character presently to be described which includes a base and a stored energy means for forming in conjunction with the base a fluid reservoir for containing medicinal fluids to be controllably infused into a patient.

As best seen by referring to FIG. 1, the fill assembly of this form of the invention comprises a container subassembly 14, an adapter assembly 15, and a cover subassembly 17, the character of which will presently be described. Container subassembly 14 includes a body portion 16, having a fluid chamber 18 for containing an injectable fluid "F" provided with first and second open ends 20 and 22 (FIGS. 2 and 3). First open end 20 is sealably closed by closure means here provided in the form of a pierceable septum assembly 24. Septum assembly 24 is held securely in position by a clamping ring 24a. As best seen in FIGS. 2 and 3, a plunger 26 is telescopically movable within chamber 18 of container subassembly 14 from a first location shown in FIG. 2 where it is proximate first open end 22 to a second position shown in FIG. 3 where it is proximate first open end 20. The vial portion of container subassembly 14 can be constructed from various materials such as glass and plastic.

Referring particularly to FIG. 1, it can be seen that the adapter subassembly 15 comprises a hollow housing 30 having a first open end 32 and a second closed end 34 (FIG. 3). Container subassembly 14 is telescopically receivable within open end 32 of housing 30 in the manner shown in FIG. 3 so that the housing can be moved from the first extended position shown in FIG. 2 to the second vial encapsulation position shown in FIG. 3. Forming an important part of the adapter subassembly is pusher means shown here as an elongated pusher rod 36 which functions to move plunger 26 within fluid chamber 18 from the first position shown in FIG. 2 to the second position shown in FIG. 3. In the form of the invention shown in the drawings, pusher rod 36 has a first end 36a interconnected with closure wall 34 and an opposite end 36b which engages plunger 26 and causes telescopic movement of the plunger within chamber 18 of container subassembly 14 as housing 30 is moved from the extended position into the vial encapsulating position shown in FIG. 3.

As best seen by referring to FIG. 4, the interior wall 31 of housing 30 is provided with circumferentially spaced-apart protuberances 40 which engage and center container subassembly 14 within housing 30. Due to the small surface area presented by protuberances 40, there is little frictional resistance to the sliding movement of container subassembly 14 relative to housing 30 as the housing is moved from the extended position shown in FIG. 2 into the vial encapsulating position shown in FIG. 3.

Cover subassembly 17 of the fill assembly of the present form of the invention includes a spiral wound frangible portion 42 having a first open end 44 for telescopically receiving body portion 16 of container subassembly 14 (FIG. 2) and a second closed end 46. Portion 42 initially circumscribes a major portion of container subassembly 14 in the manner best seen in FIG. 2. An integral pull tab 42a is provided to permit the spiral wound portion to be pulled from container subassembly 14 so as to expose a substantial portion of body 16. As best seen in FIG. 1, a medicament label 50 circumscribes spiral wound portion 42 and serves to prevent accidental unwinding of the spiral portion from the container subassembly 14. However, upon pulling tab 42a, the spiral portion will unwind and, in so doing, will tear medicament label 50 so that the spiral portion 42 of the covering as well as a cylindrical portion 52 which, also comprises a part of the cover assembly, can be slipped from the container 14 so as to expose to view septum assembly 24.

As shown in FIGS. 1 and 2, the apertured end 52a of cylindrical portion 52 of subassembly 17 is provided with venting apertures 54 which are covered by a porous vent patch 56 which can be constructed from any suitable porous material that will permit air entrapped within the interior of cover subassembly 17 to be expelled to atmosphere as the subassembly is placed over container subassembly 14.

Turning next to FIGS. 5 through 8, one form of the fluid delivery assembly usable with the fill assembly of the invention is there illustrated and generally identified by the numeral 60. While fill assembly 12 can be used with a wide variety of different types of fluid delivery assembly, the assembly shown in FIGS. 5 through 8 is representative of one type of such fluid delivery assembly. This assembly comprises a base subassembly 62, a cover subassembly 64 receivable over base subassembly 62, and a stored energy means for forming in conjunction with base subassembly 62 a fluid reservoir (FIG. 7). In the form of the invention shown in FIGS. 5 through 8 of the drawings, the stored energy means comprises a thin elastomeric membrane 66 the periphery of which is clamped in engagement with an upraised portion 68 formed on a base member 70 by a clamping ring 72. Base subassembly 62, in addition to base member 70, includes a thin, planar shaped foam pad 71. Foam pad 71 is provided with adhesive on both its upper and lower surfaces. The adhesive on the upper surface of the pad enables the pad to be affixed to the lower surface of base member 70. As indicated in FIGS. 5 and 7, a peel strip 71a is connected to the bottom surface of foam pad 71 by the adhesive provided thereon. When the device is to be used, peel strip 71a can be stripped away from the pad so that the adhesive on the lower surface thereof can be used to releasably affix the apparatus of the invention to the patient's body.

As best seen in FIGS. 5 and 6, cover subassembly 64 includes a cover member 74 and a medicament label 65. Cover member 74 is provided with an elongated receiving chamber 76 which is adapted to receive the fill subassembly of the invention. In a manner presently to be described, the fill subassembly communicates via passageways 78, 80 and 81 with the fluid reservoir 82 which is formed between elastomeric membrane 66 and base member 70 (FIGS. 6 and 7).

Passageways 78 and 80 are formed within a housing 84 which is connected to cover member 74, while passageway 81 is formed within upraised portion 68 of base member 70. The outboard ends of passageway 80 are closed by bonded closure plugs "P". Housing 84 comprises a part of the cover subassembly of the invention and includes an outlet passageway 86 which communicates with a luer assembly 88 via flow control means generally designated by the numeral 90 (FIGS. 7 and 8A). As best seen in FIG. 8A, the flow control means here comprises an assemblage made up of four disc-like wafers. Wafers 94 and 96 of the assemblage comprise porous glass distribution frits, while intermediate wafers 98 and 100 comprise a filter member and a rate control member respectively.

While filter member 98 can be constructed from a wide variety of materials, a material comprising polysulfone sold by Gelman Sciences under the name and style of SUPOR has proven satisfactory. Rate control member 100 is preferably constructed from a porous medium such as a polycarbonate material having extremely small flow apertures ablatively drilled by an excimer laser ablation process. Both the orifice size and unit distribution can be closely controlled by this process. However, a number of other materials can also be used to construct this permeable member, including metals, ceramics, cermet, glass and plastic. The rate control member can be specifically tailored to accommodate multiple flow regimens including very low flow and intermediate flow conditions.

As best seen in FIGS. 6 and 7A, housing 84 includes a generally cylindrically shaped hollow hub-like portion 102 which extends into receiving channel 76 when the housing 84 is mated with cover member 74. Formed within hub-like portion 102 is a hollow piercing cannula 104 the purpose of which will presently be described. As indicated in FIG. 6, the internal bore of hollow cannula 104 comprises the previously identified fluid passageway 78 which is in fluid communication with flow passageway 80 of housing 84.

In using the apparatus of the invention, with the fill assembly in the filled configuration shown in FIG. 2, the cover subassembly is first removed from the container subassembly by pulling on pull-tab 42a. This will cause the spiral portion 42 of the cover subassembly to tear away from the container subassembly so that it can be separated from the forwardly disposed portion 52. Once the spiral wound portion 42 is removed, cylindrical portion 52 can also be removed and discarded. Removal of the cover subassembly exposes the forward portion of the container subassembly and readies the adapter subassembly for interconnection with the fluid delivery assembly.

Prior to mating the adapter assembly with the fluid delivery assembly, closure plug 106 of the cover subassembly must be removed in the manner illustrated in FIG. 5. This done, the fill assembly can be telescopically inserted into receiving chamber 76 and pushed forwardly in the direction indicated by the arrow 107 in FIG. 7A. A force exerted in the direction of the arrow will cause the adapter subassembly to move to the right as viewed in FIG. 7A and will cause the piercing cannula 104 to pierce septum 24. Once a fluid flow path between fluid chamber 18 of the container subassembly 16 and the fluid reservoir 82 of the fluid delivery assembly is thus created, a continued movement of the adapter subassembly will cause pusher rod 36 to move plunger 26 forwardly of chamber 18 to a position shown in FIG. 7A. As plunger 26 is moved forwardly of chamber 18, the fluid "F" contained within the chamber will flow into open end 20, through passageway 78 of the piercing cannula into passageway 80 of housing 84 and then into fluid reservoir 82 via passageway 81. As the fluid under pressure flows into reservoir 82, membrane 66 will be distended outwardly in the manner shown in FIG. 7 to a position where it engages inner wall 74a of cover member 74. Ring 72, which is in clamping engagement with upstanding portion 68 of base 70 functions to capture and seal the membrane against portion 68 and prevent leakage of fluid around the perimeter of the membrane. A vent means shown as vent port "V" is provided in cover member 74 for venting of gases between the membrane and inner wall 74a to atmosphere.

It is to be understood that membrane 66 can comprise a single film layer or can comprise a laminate construction made up of a number of cooperating layers. In this regard, reference should be made to columns 10 and 11 of U.S. Pat. No. 5,411,480 which patent is incorporated herein by reference, wherein the various materials that can be used to construct membrane 66 are discussed in detail. Reference should also be made to columns 11 and 12 of this patent for the various materials that can be used in the construction of the cover and base subassemblies of the fluid delivery apparatus of the present invention. Reference to FIG. 39 of the patent will show a distendable membrane of a laminate construction that can be used in the construction of the fluid delivery assembly of the present invention (see also columns 17 and 18 of U.S. Pat. No. 5,411,480).

Referring particularly to FIG. 7, it is to be noted that reservoir 82 is provided with a second fluid inlet 112 which communicates with a fluid passageway 111. Inlet 112 is sealably closed by an elastomeric pierceable member 114 which can be pierced by fluid delivery means well known in the art, such as a hypodermic syringe 115, so that a second fluid or other additive can be added to reservoir 82. The selected additive can be added to the reservoir either prior to or subsequent to the filling of the reservoir through use of the fill assembly in the manner described in the preceding paragraphs. In this regard, reference should be made to column 21 of incorporated by reference U.S. Pat. No. 5,411,480 for a complete definition of the terms additive and adding means. Forming a part of the adding means of this invention, in addition to the filling syringe 115 (FIG. 7) is a functional support 116 which is of the character more completely defined in incorporated U.S. Pat. No. 5,411,480. By way of example, functional support 116 can take the form of any one of the functional supports illustrated in FIG. 45 of the incorporated patent and described therein.

Once reservoir 82 is filled either with fluid from the container subassembly of the fill assembly, or from the adding means, or by a combination of both, the fluid will remain in the reservoir until such time as the luer cap 89 is removed from luer assembly 88 so as to open the outlet flow path of the fluid delivery assembly. Once the outlet flow path 120 of the assembly is opened, distendable membrane 66 will tend to return to its less distended configuration causing fluid to flow from reservoir 82 outwardly through flow passageways 81 and 86 and then into the outlet port 120 of the device via the flow control means 90.

Referring particularly to FIGS. 1 and 7A, it is to be noted that hollow housing 30 includes locking means for locking the housing within receiving chamber 76 of cover 74 after the fill subassembly has been mated with the fluid delivery assembly. These locking means are here provided in the form of a series of locking teeth 122 and 124 respectively. As indicated in FIG. 7A, these locking teeth and constructed so that they will slide under a flexible locking tab 126, which is provided proximate the entrance of receiving chamber 76, as the adapter subassembly is urged inwardly of receiving chamber 76. However, once the adapter subassembly has reached the fully inserted position shown in FIG. 7A, wherein the fluid "F" is transferred to reservoir 82, locking tab 126 will effectively prevent removal of housing 30 of the adapter subassembly from passageway 76. With this novel construction, once reservoir 82 has been filled with the fluid contained in the container subassembly, the adapter assembly cannot be removed from the fluid delivery device and, therefore, cannot be reused thereby preventing system adulteration.

Also forming an important aspect of the present invention is the provision of viewing means for viewing at any time the volume of fluid contained within chamber 18 of the fluid container subassembly 14. In the form of the invention shown in the drawings, this viewing means takes the form of an elongated viewing window 130 which is provided in housing 30 (FIG. 1). As indicated in FIG. 1, the body portion 16 of the container subassembly is provided with a plurality of longitudinally spaced-apart index lines, or marks 132, which can be viewed through window 130 as the container subassembly is urged forwardly of housing 30 in the manner previously described. Index lines 132 provide reference points for observing the volume of fluid remaining within the container subassembly.

Referring next to FIGS. 9 through 10A, another embodiment of the present invention is there illustrated. This embodiment is similar in many respects to the embodiment shown in FIGS. 1 through 8 and, accordingly like numbers have been used to identify like components. The primary difference between this latest form of the invention and that previously described herein is that the stored energy source, rather than comprising a distendable membrane, here uniquely comprises an expandable mass such as a cellular mass of the character designated in the drawings by the numeral 150 (FIGS. 9 and 10).

As before, the fluid delivery apparatus, with which the fill assembly 12 is usable, comprises a base subassembly 62, a cover subassembly 64 receivable over base subassembly 62, and the earlier identified stored energy means for forming in conjunction with base subassembly 62 a fluid reservoir. As previously mentioned, the stored energy means here comprises a resiliently, compressible and expandable cellular mass 150 which, as best seen in FIG. 9, overlays upraised portion 68 of base member 70. Disposed between the upper surface 68a of portion 68 and the lower surface 150a of cellular mass 150 is a barrier member 154, the purpose of which will presently be described.

Cover 64 is provided with an elongated receiving chamber 76 which is adapted to receive the fill assembly of the invention. As before, the fill assembly communicates via passageway 78, 80 and 81 with a fluid reservoir 156 which, as best seen in FIG. 10A, is formed between barrier member 154 and the upper surface 68a of portion 68.

Passageways 78 and 80 are formed within a housing 84 which is of identical construction to that previously described. As before, housing 84 also includes an outlet passageway 86 which communicates with a luer assembly 88 via flow control means 90 which are also identical to that previously described.

In using the apparatus of this latest form of the invention, with the fill assembly in the filled configuration shown in FIG. 2, the cover subassembly is first removed from the container subassembly in the manner previously described. The closure plug 106 of the cover subassembly is next removed and the fill assembly is telescopically inserted into receiving chamber 76 in the same manner as previously described and pushed forwardly to cause the piercing cannula 104 to pierce septum 24. Once a fluid flow path between chamber 18 of container subassembly 16 and reservoir 156 (FIG. 10A) is opened, a continued movement of the adapter subassembly will cause pusher rod 36 to move plunger 26 forwardly of chamber 18. As plunger 26 is moved forwardly of chamber 18, as before, fluid "F" contained within the chamber will flow through passageway 78 of the piercing cannula into passageway 80 of housing 84 and then into reservoir 156 via passageway 81. As the fluid under pressure flows into chamber 157 below member 154, it will impinge upon member 154 causing the member to distend outwardly in the manner shown in FIG. 10A to form reservoir 156. As member 154 distends outwardly, it will uniformly deform the stored energy means, or cellular mass 150 against inner wall 74a of cover member 74. Ring 72, which is in clamping engagement with upstanding portion 68 of base 70 functions to seal the barrier member 154 against portion 68 and prevent leakage of fluid around the perimeter of the member.

It is to be understood that cellular mass 150 as well as barrier member 154 can be constructed from a wide variety of materials. In this regard, reference should be made to column 43 of U.S. Pat. No. 5,411,480 which patent is incorporated herein by reference, wherein the various materials that can be used to construct an elastic, compressible mass, such as cellular mass 150 are discussed in detail. As to barrier member 154 this member can be constructed from any suitable deformable barrier film and, if desired, can be constructed from a number of suitable elastomers of the same general character as those used to construct distendable membrane 66. Other barrier materials can include: Krayton (tradename), styrene-butadien-styrene block copolymer (chemical name), sold by Shell Chemical Company; Urethane sold by Argotec; Polyester, sold by Eastman Kodak, DuPont, Hoechst; Barex, sold by British Petroleum; Elastomers such as fluoroelastomers, fluorosilicone, sold by 3M and Austnont; Saran-HB (tradename), polyester/ polyadipate copolymer, sold by Dow Chemical; Eypal-F (tradename), polyphophazine fluoroelastomer, sold by Ethyl Corp., Gulf South Research Institute or Hygienic; Isobutylene-isoprene, sold by Polysar, Inc.; Neoprene (tradename), polychloroprene latex (chemical name), sold by DuPont.

Referring particularly to FIGS. 9 and 10A, it is to be noted that reservoir 156 is provided with a second fluid inlet 111 which communicates with a fluid passageway 112. Inlet 111 is sealably closed by an elastomeric pierceable member 114 which, as before, can be pierced by fluid delivery means well known in the art, such as a hypodermic syringe 115, so that a second fluid or other additive can be added to reservoir 156 in the manner previously described. Once again, reference should be made to column 21 of incorporated by reference U.S. Pat. No. 5,411,480 for a complete definition of the terms additive and adding means. Forming a part of the adding means of this latest form of the invention, in addition to the filling syringe 115 (FIG. 10A) is a functional support 116 which is of the character more completely defined in incorporated U.S. Pat. No. 5,411,480.

Once reservoir 156 is filled either with fluid from the container subassembly of the fill assembly, or from the adding means, or by a combination of both, the fluid will remain in the reservoir until such time as the luer cap 89 is removed from luer assembly 88 so as to open the outlet flow path of the fluid delivery assembly. Once the outlet flow path of the assembly is opened, cellular mass 150 will controllably expand causing fluid to flow from reservoir 156 outwardly through flow passageways 81 and 86 and then into the outlet port 120 of the device via the flow control means 90.

As before, locking means of the character previously described are provided for locking housing 30 within receiving chamber 76 of cover 74 after the fill assembly has been mated with the fluid delivery assembly.

Also provided in this latest form of the invention is viewing means of the character previously described for viewing at any time the volume of fluid "F" contained within chamber 18 of the fluid container subassembly 14.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fill assembly for use with a fluid delivery apparatus including a base having a receiving chamber having a pierceable cannula and a stored energy means for forming, in conjunction with the base, a fluid reservoir having an inlet in communication with said piercing cannula, and an outlet, said stored energy means being adapted to expel fluid from the fluid chamber, said fill assembly comprising:
    (a) a container subassembly including:
        (i) a container having a body portion provided with spaced-apart indicia, said body portion having a fluid chamber and first and second open ends;
        (ii) closure means for sealably closing said first open end of said container, said closure means comprising a pierceable septum adapted to be pierced by the piercing cannula of the base; and
        (iii) a plunger telescopically movable within said container from a first location proximate said second open end to a second, spaced-apart location;
    (b) an adapter subassembly comprising a hollow housing adapted to be received within the receiving chamber of the base of the fluid delivery apparatus, said hollow housing having a first open end for telescopically receiving said container of said container subassembly and a second closed end, said hollow housing further including pusher means for engagement with said plunger to move said plunger within said container toward said second location; and
    (c) a cover subassembly including a cover having a first open end for telescopically receiving a part of said body portion of said container of said container subassembly and a second end, said cover being removable from said container to expose said closure means.

2. A fill assembly as defined in claim 1 in which said hollow housing of said adapter assembly includes a window for viewing said spaced apart indicia on said body portion of said container of said container subassembly.

3. A fill assembly as defined in claim 1 in which said hollow housing of said adapter assembly includes locking means for locking said hollow housing to the fluid delivery apparatus.

4. A fill assembly as defined in claim 1 in which said cover of said cover subassembly comprises a spiral would frangible portion.

5. A fill assembly as defined in claim 4 further including a medicament label circumscribing said spiral wound frangible portion.

6. A fill assembly as defined in claim 4 in which said container comprises a glass vial and in which said container subassembly further includes means for connecting said pierceable septum to said glass vial.

7. A fill assembly adapted for use with a fluid delivery apparatus of the character having a base and a stored energy means for forming, in conjunction with the base, a fluid reservoir having an inlet and an outlet, said stored energy means being adapted to expel fluid from the fluid chamber, said fill assembly comprising:
    (a) a container subassembly including:
        (I) a container having a body portion, a fluid chamber, and first and second open ends;
        (ii) closure means for sealably closing said first open end of said container, said closure means comprising a pierceable septum; and
        (iii) a plunger telescopically movable within said container from a first location proximate said second open end to a second, spaced-apart location;
    (b) an adapter subassembly comprising a hollow housing having a first open end for telescopically receiving said container and a second closed end, said hollow housing further including pusher means for engagement with said plunger to move said plunger within said container toward said second location; and
    (c) cover subassembly including a cover having a first open end for telescopically receiving a part of said body portion of said container of said container subassembly and a second end including vent means for venting gases within said cover to atmosphere as said part of said body portion of said container subassembly is telescopically received within said cover.

8. A fill assembly as defined in claim 7 in which said cover is removable from said container to expose said closure means.

9. A fill assembly as defined in claim 7 in which said adapter subassembly further includes means for viewing fluid within said fluid chamber of said container of said container subassembly.

10. A fill assembly as defined in claim 7 in which cover includes a spiral wound frangible portion.

11. A fill assembly as defined in claim 10 in which said cover subassembly further includes a medicament label circumscribing said spiral wound frangible portion.

12. A fill assembly adapted for use with a fluid delivery apparatus of the character having a base and a stored energy means for forming, in conjunction with the base, a fluid reservoir having an inlet and an outlet, said stored energy means being adapted to expel fluid from the fluid chamber, said fill assembly comprising:
    (a) a container subassembly including:
        (i) a container having a body portion, a fluid chamber, and first and second open ends;
        (ii) closure means for sealably closing said first open end of said container; and
        (iii) a plunger telescopically movable within said container from a first location proximate said second open end to a second, spaced-apart location; and
    (b) an adapter subassembly comprising a hollow housing having a first open end for telescopically receiving said container and a second closed ends said hollow housing further including:
  (i) pusher means for engagement with said plunger to move said plunger of said container subassembly to move said plunger within said container toward said second location; and
  (ii) locking means for locking said hollow housing to the fluid delivery apparatus.

13. An apparatus for delivering fluid at a controlled rate comprising:
  (a) a fluid delivery assembly comprising:
    (i) a base; and
    (ii) a cover connected to said base, one of said cover and said base having a receiving chamber; and
    (iii) stored energy means for forming in conjunction with said base a fluid reservoir having an inlet in communication with said receiving chamber, said stored energy means functioning to act upon fluids contained within said fluid reservoir to controllably expel said fluids from the fluid delivery assembly; and
  (b) a fill assembly interconnected with said fluid delivery assembly comprising:
    (i) a container subassembly including:
      a. a container having a body portion, a fluid chamber, and first and second open ends;
      b. closure means for sealably closing said first open end of said container; and
      c. a plunger telescopically movable within said container from a first location proximate said second open end to a second, spaced-apart location;
    (ii) an adapter subassembly comprising a hollow housing having a first open end for telescopically receiving a part of said body portion of said container of said container subassembly and a second end, said hollow housing further including pusher means for engagement with said plunger to move said plunger within said container between said first and second locations.

14. An apparatus as defined in claim 13 in said fill assembly further includes a cover subassembly including a cover having a first open end for telescopically receiving a part of said body portion of said container of said container subassembly and a second end, said cover being removable from said container to expose said closure means.

15. An apparatus as defined in claim 13 in which said stored energy means of said fluid delivery assembly comprises an elastomeric membrane.

16. An apparatus as defined in claim 13 in which said stored energy means of said fluid delivery assembly comprises an expandable mass.

17. An apparatus as defined in claim 13 in which said closure means of said container subassembly comprises a pierceable septum.

18. An apparatus as defined in claim 13 further including adding means in communication with said reservoir for adding an additive to fluid flowing toward said fluid reservoir.

19. An apparatus for delivering fluid at a controlled rate comprising:
  (a) a fluid delivery assembly comprising:
    (i) a base including a piercing cannula; and
    (ii) a cover receivable over to said base, said cover including a receiving chamber; and
    (iii) stored energy means for forming in conjunction with said base a fluid reservoir having an inlet in communication with said receiving chamber of said cover, said stored energy means functioning to act upon fluids contained within said fluid reservoir to controllably expel said fluids from the fluid delivery device; and
  (b) a fill assembly interconnected with said fluid delivery assembly comprising:
    (i) a container subassembly including:
      a. a container having a body portion provided with spaced-apart indicia, said body portion having a fluid chamber, and first and second open ends;
      b. closure means for sealably closing said first open end of said container, said closure means comprising a pierceable septum adapted to be pierced by the piercing cannula of the base; and
      c. a plunger telescopically movable within said container from a first location proximate said second open end to a second, spaced-apart location;
    (ii) an adapter subassembly comprising:
      a hollow housing adapted to be received within the receiving chamber of the base of the fluid delivery apparatus, said hollow housing having a first open for telescopically receiving said container of said container subassembly and a second closed end, said hollow housing further including pusher means for engagement with said plunger to move said plunger within said container toward said second location; and
    (iii) a cover subassembly including a cover having a first open end for telescopically receiving a part of said body portion of said container of said container subassembly and a second end, said covering being removable from said container to expose said closure means.

20. An apparatus as defined in claim 19 in which said hollow housing of said adapter assembly includes a window for viewing said spaced-apart indicia on said body portion of said container of said container subassembly.

21. An apparatus as defined in claim 19 in which said hollow housing of said adapter assembly includes locking means for locking said hollow housing to the fluid delivery apparatus.

22. An apparatus as defined in claim 19 in which said stored energy means of said fluid delivery device comprises an elastomeric membrane.

23. An apparatus as defined in claim 19 in which said stored energy means of said fluid delivery device comprises an expandable mass.

\* \* \* \* \*